United States Patent
Evans et al.

(10) Patent No.: US 7,854,712 B2
(45) Date of Patent: Dec. 21, 2010

(54) KNITTED SUBSTRATE FOR USE IN MEDICAL BANDAGING PRODUCT, BANDAGING PRODUCT AND METHOD OF FORMING THE SAME

(75) Inventors: John C. Evans, Charlotte, NC (US); Keith Clapham, Nelson (GB)

(73) Assignee: BSN Medical, Inc., Wilmington, DE (US)

( * ) Notice: Subject to any disclaimer, the term of this patent is extended or adjusted under 35 U.S.C. 154(b) by 1155 days.

(21) Appl. No.: 10/478,525

(22) PCT Filed: May 30, 2002

(86) PCT No.: PCT/GB02/02275
§ 371 (c)(1),
(2), (4) Date: May 20, 2004

(87) PCT Pub. No.: WO02/096332
PCT Pub. Date: Dec. 5, 2002

(65) Prior Publication Data
US 2004/0193083 A1 Sep. 30, 2004

(30) Foreign Application Priority Data
May 31, 2001 (GB) .................................. 0113119.2

(51) Int. Cl.
*A61F 5/00* (2006.01)
*D04B 7/04* (2006.01)

(52) U.S. Cl. .............. 602/6; 602/1; 602/5; 66/196; 66/192; 66/193; 66/195

(58) Field of Classification Search .............. 602/6, 602/8, 1, 5; 442/312, 313, 311; 66/192, 66/193, 195, 202, 196
See application file for complete search history.

(56) References Cited

U.S. PATENT DOCUMENTS

| 2,960,984 | A |   | 11/1960 | Parker |
|-----------|---|---|---------|--------|
| 4,015,451 | A | * | 4/1977  | Gajjar .......................... 66/195 |
| 4,572,171 | A |   | 2/1986  | Wegner et al. |
| 5,003,970 | A |   | 4/1991  | Parker et al. |
| 5,133,199 | A | * | 7/1992  | Parikh et al. .................. 66/192 |

(Continued)

FOREIGN PATENT DOCUMENTS

WO    WO 99 62440    12/1999

(Continued)

*Primary Examiner*—Patricia M Bianco
*Assistant Examiner*—Tarla R Patel
(74) *Attorney, Agent, or Firm*—Adams Intellectual Property Law

(57) ABSTRACT

A medical bandaging product having a predetermined length suitable for a given medical use, including an enclosure formed of a moisture-impervious material sealable to prevent entry of moisture and a medical bandage material positioned in the enclosure and sealed therein against entry of moisture until use. The medical bandage material includes a substrate formed from a single integrated knitted fabric layer having a plurality of interconnected knitted fabric yarns forming a three-dimensional structure. A reactive system is impregnated into or coated onto the substrate. The system remains stable when maintained in substantially moisture-free conditions and hardens upon exposure to sufficient moisture to cooperate with the three-dimensional structure to form a rigid, self supporting structure. A soft, flexible protective wrapping encloses the substrate along its length for providing a cushioning barrier interposed between the substrate and a patient when the medical bandage material is in use.

25 Claims, 18 Drawing Sheets

U.S. PATENT DOCUMENTS

| | | | |
|---|---|---|---|
| 5,461,885 A * | 10/1995 | Yokoyama et al. | 66/170 |
| 5,514,080 A | 5/1996 | Blott et al. | |
| 5,520,621 A | 5/1996 | Edenbaum et al. | |
| 5,755,678 A * | 5/1998 | Parker et al. | 602/6 |
| 5,807,295 A | 9/1998 | Hutcheon et al. | |
| 6,007,505 A | 12/1999 | Grim et al. | |
| 6,139,513 A | 10/2000 | Grim et al. | |
| 6,186,966 B1 | 2/2001 | Grim et al. | |
| 6,290,663 B1 | 9/2001 | Darcey | |
| 6,461,317 B1 | 10/2002 | Grim et al. | |
| 6,477,865 B1 * | 11/2002 | Matsumoto | 66/195 |
| 6,719,710 B2 * | 4/2004 | Darcey | 602/8 |
| 2002/0035343 A1 * | 3/2002 | Darcey | 602/8 |
| 2002/0161318 A1 * | 10/2002 | Pounder et al. | 602/6 |

FOREIGN PATENT DOCUMENTS

| | | | |
|---|---|---|---|
| WO | | 0135874 A1 | 5/2001 |
| WO | WO 01 35874 | | 5/2001 |

* cited by examiner

KNITTED SUBSTRATE FOR USE IN MEDICAL BANDAGING PRODUCT, BANDAGING PRODUCT AND METHOD OF FORMING THE SAME

CROSS-REFERENCE TO RELATED APPLICATIONS

This application is a National Stage application of International Patent Application No. PCT/GB02/02275, filed May 30, 2002.

TECHNICAL FIELD AND BACKGROUND OF THE INVENTION

This invention relates generally to the field of orthopedic medicine and more specifically to the design of an improved medical bandaging product and material which includes a warp knitted, double-layered fabric substrate, a method for constructing such an improved bandaging product, and a method of constructing and applying an improved bandaging product.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time consuming. Several components are required and considerable skill is necessary.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of casting and splinting is disclosed in U.S. Pat. Nos. 4,411,262 and 4,502,479. The casting materials disclosed in these patents include bandaging materials which incorporate a substrate formed from a plurality of flexible fabric layers, such as fiberglass, impregnated with a moisture-curing resin. These bandaging materials are enclosed in a moisture-free, moisture-impervious package until use. Compared to plaster-of-paris, these products are extremely lightweight, have a very high strength to weight ratio and can be made relatively porous, permitting a flow of air through the casting material. However, no provision has been made for moisture-curing systems which incorporate a substrate which is formed from a single layer of fabric, yet is strong and absorbent enough to be impregnated with amounts of moisture-curing resin comparable to those amounts absorbed by conventional multi-layered substrates.

U.S. Pat. Nos. 4,770,299 and 5,003,970, among others owned by applicant, each disclose roll-form synthetic bandaging products which include the ability to dispense desired lengths of bandaging material when needed, while sealing the remaining length of material for later use. Similar products are also sold in precut lengths sealed in a single use, moisture-impervious envelope. Although these products have proven to be very successful in many applications, each product is formed using multi-layered substrate materials.

Both the conventional plaster-of-paris casting method and the more recent moisture-curable resin casting method possess certain disadvantages. Plaster-of-paris casts are bulky, heavy and difficult to apply. Even though moisture-curable resin bandage products are lightweight, durable and relatively easy to apply, such products remain relatively expensive to produce.

This invention combines the advantages of both plaster-of-paris and moisture-curable resin systems while avoiding their respective disadvantages. This is accomplished by providing a unitary splinting system which incorporates moisture-curable resin materials formed from a resin-impregnated substrate having both a lighter weight and improved strength. Unlike prior art resin systems which employ multiple layers of resin-impregnated substrate layers, the resin system of the present invention takes advantage of a single layer of warp-knitted fabric. This unique substrate fabric employs a continuous inlaid stitch. This results in a double-knitted fabric which has a lighter weight, yet retains the absorption capabilities of multi-layered substrates. Using a single layer of double-knitted fabric in the substrate further results in reduced production and labor costs in comparison with other synthetic cast products. For example, assembly of prior art, multi-layered substrates requires placement of the overlying fabric layers of the substrate by hand, which is a time consuming process. To ensure that the fabric layers do not separate, the layers must then be stitched together by running one or more seams along the entire length of the substrate. Use of a substrate having only one layer eliminates these labor-intensive layering and stitching steps, and results in a bandaging product which is more cost effective to produce.

Eliminating the multi-layered substrate structure also eliminates the rough, uneven edges present on prior art cured substrates. Such frayed edges are commonplace in prior art bandaging products having multi-layered substrates, and materialize after the resin in such substrates undergoes final curing. These rough edges cause irritation and damage to the skin of the patient upon whom the bandage is ultimately applied. In contrast, the substrate of the present invention has uniform side edges which result from using the single-layer of double-knitted fabric, rather than multiple, uneven fabric layers. This novel structure results in a medical bandage product having a moisture-curable substrate which is lighter in weight than conventional products, yet is stronger and more cost-effective to produce.

SUMMARY OF THE INVENTION

It is therefore an object of the invention to provide a medical bandaging product having a medical material that includes a substrate formed from a single layer of double-knitted fabric capable of absorbing an increased amount of a moisture-curable resin which hardens the bandaging material upon exposure to moisture to form a rigid, self-supporting structure.

It is another object of the invention to provide a medical bandaging product including a medical bandaging material formed from a resin-impregnated substrate having a knitted structure that provides enhanced strength to the bandaging material after the resin is cured without compromising flexibility of the material prior to curing.

It is another object of the invention to provide a medical bandage material which can be dispensed in any desired length while preventing hardening of the remaining material until use of the remaining material is desired.

It is another object of the invention to provide a medical bandage material having a medical material that includes a resin-impregnated substrate possessing a relatively high strength to weight ratio resulting in a finished splint which is lighter and less bulky than splints using conventional plaster-of-paris or moisture-curable resin systems.

It is another object of the invention to provide a medical bandaging product having a medical bandage material which incorporates a substrate formed from a single layer of double-knitted fabric, thereby eliminating the formation of rough, uneven side edges which commonly form on conventional multi-layered, moisture curable substrates after the curing process is complete.

It is another object of the invention to provide a medical bandaging product which can be manufactured and sold in pre-cut lengths, each of which is sealed within a moisture-impervious package to prevent hardening of the product until use is desired.

It is another object of the invention to provide a medical bandaging product which is less labor-intensive, and thus more cost effective, to produce than conventional bandaging products that incorporate multi-layered substrates.

These and other objects and advantages of the present invention are achieved in the preferred embodiment disclosed below by providing a medical bandaging product having a predetermined length suitable for a given medical use. The medical bandaging product includes an enclosure formed of a moisture-impervious material sealable to prevent entry of moisture. A medical bandage material is positioned in the enclosure and sealed therein against entry of moisture until use. The medical bandage material includes a substrate formed from a single integrated knitted fabric layer having a plurality of interconnected knitted fabric forming a three-dimensional structure. A reactive system is impregnated into or coated onto the substrate. The reactive system remains stable when maintained in substantially moisture-free conditions and hardens upon exposure to sufficient moisture to cooperate with the three-dimensional structure to form a rigid, self supporting structure. A soft, flexible protective wrapping encloses the substrate along its length for providing a cushioning barrier interposed between the substrate and a patient when the medical bandage material is in use.

According to one preferred embodiment of the invention, the moisture-impervious material is an aluminum foil laminate having an outer tear resistant layer, a central aluminum foil layer and an inner heat sealable plastic layer.

According to another preferred embodiment of the invention, the protective wrapping enclosing the substrate is a fibrous non-woven material.

According to yet another preferred embodiment of the invention, the protective wrapping enclosing the substrate is a non-woven polypropylene sheet folded along its longitudinal axis to define an envelope within which the substrate is positioned.

According to yet another embodiment of the invention, the reactive system is synthesized from a blended polyisocyanate, polyol, catalyst and stabilizer.

According to yet another preferred embodiment of the invention, a medical bandaging product is provided in roll form for being dispensed in predetermined lengths suitable for a given medical use. The medical bandaging product includes an elongate sleeve formed of moisture-impervious material and sealable to prevent entry of moisture. An elongate medical bandage material substantially the same length as the sleeve is positioned in the sleeve in a single length along the length of the sleeve and sealed therein against entry of moisture until use. The medical bandage material includes a substrate formed from a single integrated knitted fabric sheet having plurality of interconnected knitted fabric layers forming a three-dimensional structure. A reactive system is impregnated into or coated onto the substrate. The reactive system remains stable when maintained in substantially moisture-free conditions and hardens upon exposure to sufficient moisture to cooperate with the three-dimensional structure to form a rigid, self-supporting structure. A soft, flexible protective wrapping encloses the substrate along its length for providing a cushioning barrier interposed between the substrate and a patient when the medical bandage material is in use. The medical bandage material is positioned in the enclosure for being dispensed in a desired use length from the sleeve, and the sleeve is adapted for being resealed to prevent moisture from entering the enclosure.

According to yet another preferred embodiment of the invention, the medical bandaging product includes resealing means for resealing the sleeve against entry of moisture after a predetermined length of the bandaging product has been dispensed for use to prevent hardening of the substrate remaining in the sleeve.

According to yet another preferred embodiment of the invention, the resealing means for resealing the sleeve is selected from a group which includes tape, a clamp, and a clip for holding a folded end of the sleeve closed.

According to yet another preferred embodiment of the invention, the sleeve and the medical bandage material positioned therein are formed into a coil, thereby creating the roll form of the medical bandaging product.

According to yet another preferred embodiment of the invention, the medical bandaging product includes a dispenser within which the coil is contained.

According to yet another preferred embodiment of the invention, the dispenser includes a container within which the coil is positioned. The container defines a slot therein in which a leading end of the coil may be positioned and through which the sleeve and the medical bandage positioned therein are dispensed as needed.

An embodiment of the method of constructing a medical bandaging product according to the invention includes the step of providing an elongate, moisture-impervious sleeve and an elongate medical bandage material formed from a substrate enclosed within a protective wrapping. The substrate is formed from a single integrated knitted fabric sheet having a plurality of interconnected fabric layers forming a three-dimensional structure. The method further includes the step of impregnating into or coating onto the substrate a reactive system which remains stable when maintained in substantially moisture-free conditions and hardens upon exposure to sufficient moisture to cooperate with the three-dimensional structure form a rigid, self-supporting structure. A length of the elongate medical bandaging material is then positioned within the elongate sleeve. The elongate medical bandage material has generally the same length as the sleeve and extends along the length of the sleeve in a single layer. The sleeve is then sealed to prevent entry of moisture therein until use.

According to one preferred embodiment of the invention, the method includes the step of providing a moisture impervious sleeve and a substrate for being enclosed within a protective wrapping. The substrate is formed from a single integrated knitted fabric sheet having a plurality of overlaid knitted fabric yarns forming a three-dimensional structure. The method further includes the step of impregnating into or coating onto the substrate a reactive system which remains stable when maintained in substantially moisture-free conditions and hardens upon exposure to sufficient moisture to cooperate with the three-dimensional structure to form a rigid, self-supporting structure. The coated or impregnated substrate is then positioned within the protective wrapping to form a medical bandage material. A length of the medical bandage material having generally the same length as the sleeve is then positioned within the sleeve and extends along the length of the sleeve in a single layer. The sleeve is then sealed to prevent entry of moisture until use.

According to another preferred embodiment of the invention, the method includes the step of resealing the sleeve against entry of moisture after a predetermined length of the bandaging material has been dispensed for use to prevent hardening of the substrate remaining in the sleeve.

According to yet another preferred embodiment of the invention, the method further includes the step of rolling the sleeve with the medical bandage material therein into a coil.

According to yet another preferred embodiment of the invention, the method further includes the step of packaging the coil in a dispenser.

According to yet another preferred embodiment of the invention, the dispenser provided is a box having with a slot therein for feeding a desired length of the medical bandaging material therethrough.

A further embodiment of the method according to the invention is a method of utilizing a medical bandaging product. The method includes the step of providing an enclosure and a medical bandage material. The medical bandage material includes a substrate enclosed within a protective wrapping. The substrate includes a single integrated knitted fabric sheet having a plurality of overlaid fabric layers forming a three-dimensional structure. A reactive system is impregnated into or coating onto the substrate. The reactive system remains stable when maintained in substantially moisture-free conditions and hardens upon exposure to sufficient moisture to cooperate with the three-dimensional structure to form a rigid, self-supporting structure. The method further includes the steps of positioning the elongate medical bandage material within the elongate sleeve, sealing the sleeve to prevent entry of moisture until use, removing the medical bandage material from the sleeve immediately prior to use, wetting the substrate to activate the reactive system; and applying the medical bandaging material to a patient.

According to one preferred embodiment of the method of utilizing the medical bandaging product includes the step of overwrapping the medical bandaging material with an elastic bandage to maintain the medical bandaging material in close conformity with the patient during curing of the moisture-curable resin.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENT AND BEST MODE

Figure 1:
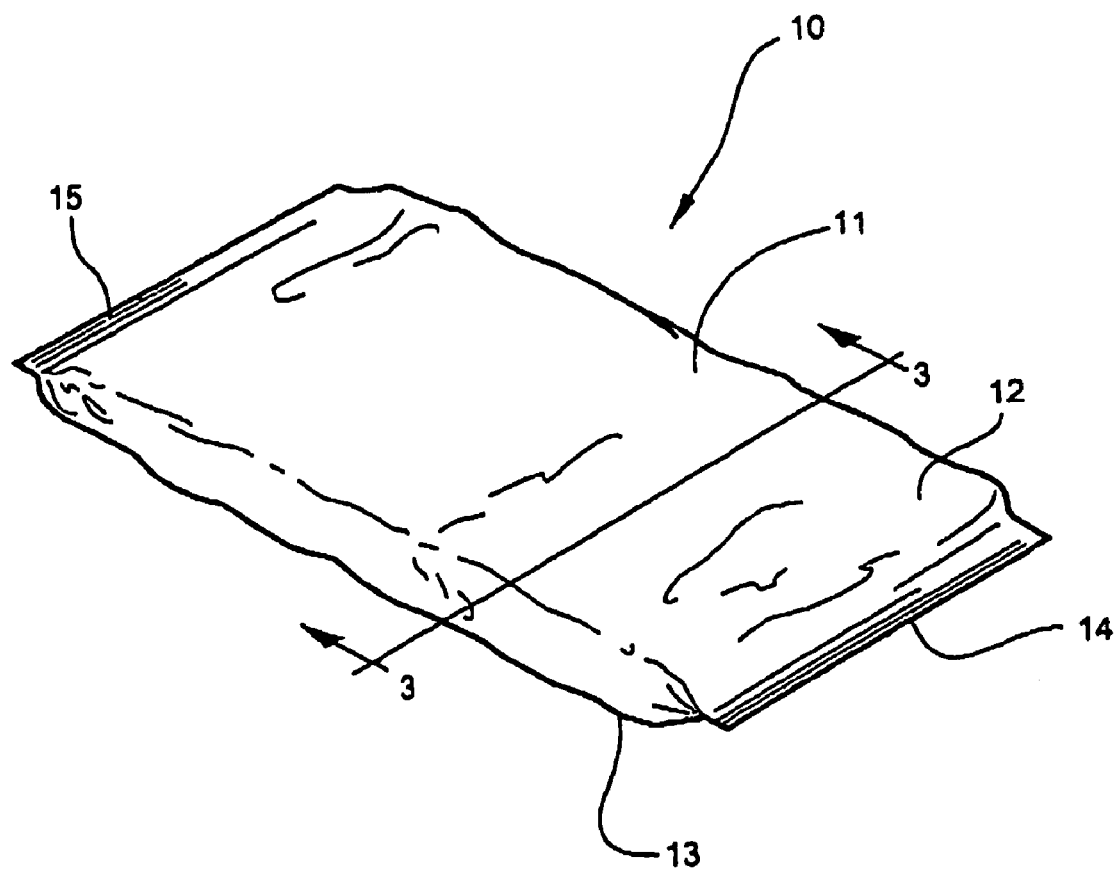
FIG. 1 is a perspective view of a medical bandaging product according to one preferred embodiment of the invention.
Figure 2:
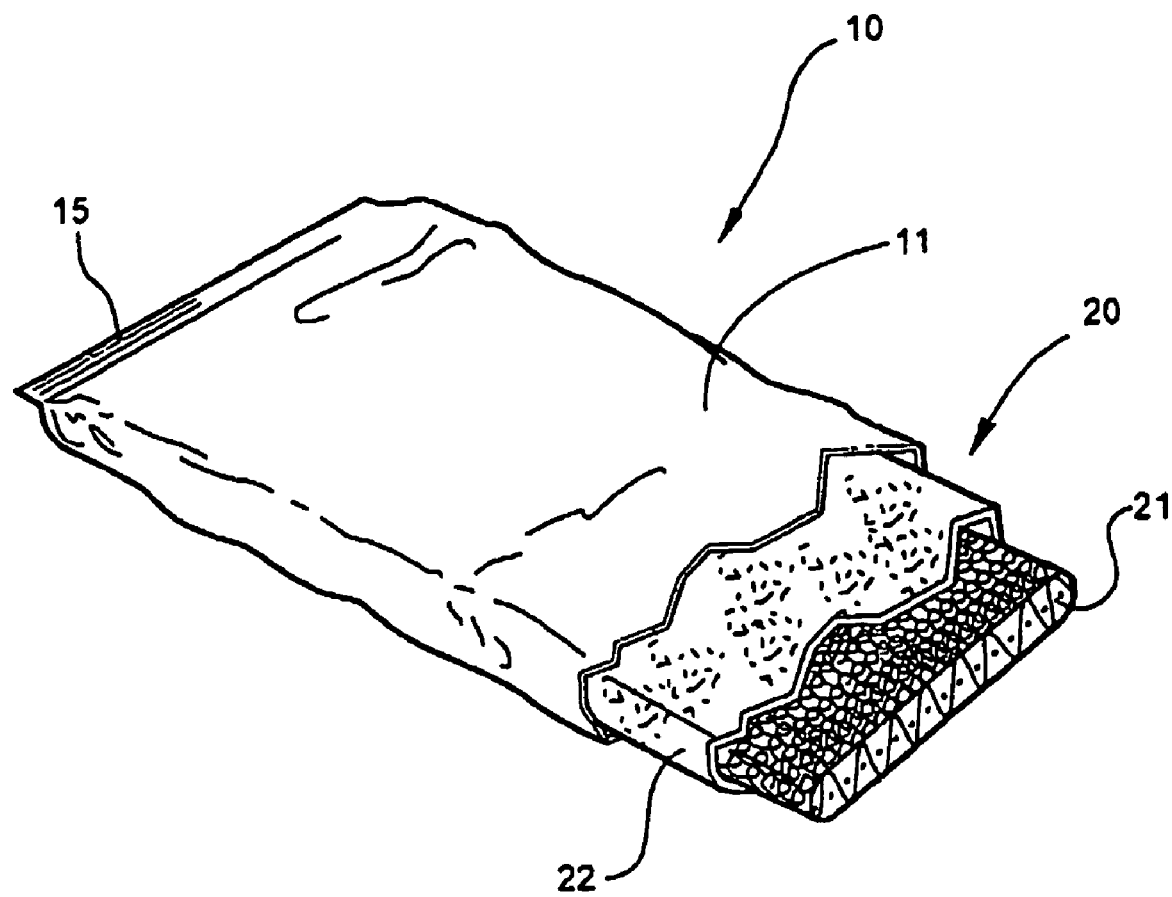
FIG. 2 is a cut-away fragmentary perspective view of the medical bandaging product shown in FIG. 1.
Figure 3:
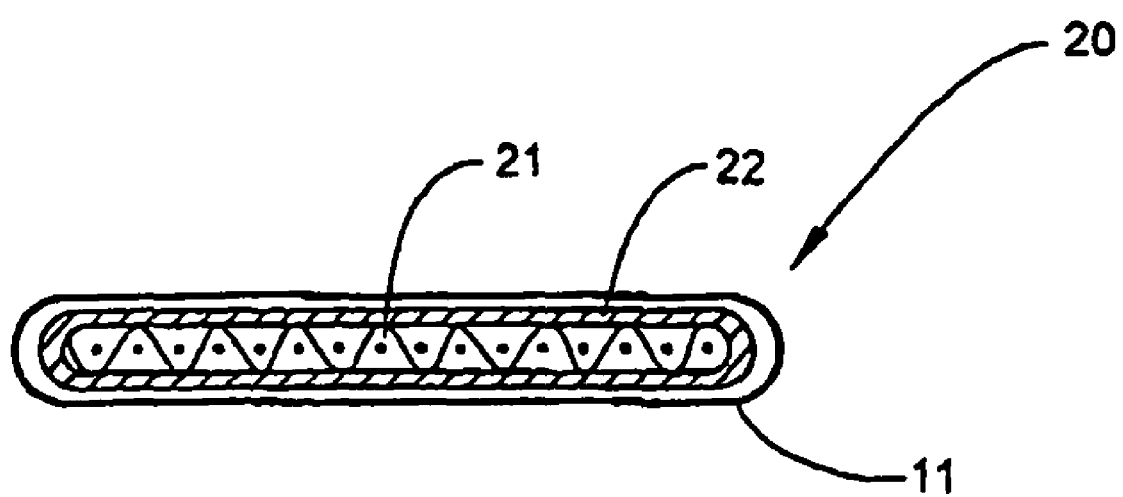
FIG. 3 is a cross-sectional view taken along lines 3-3 of FIG. 1.

Referring now specifically to the drawings, a medical bandaging product according to the present invention is shown generally in FIG. 1 at reference numeral 10. The medical bandaging product 10 includes a moisture-impervious package 11 formed from two laminated sheets 12, 13 which are placed in registration and heat sealed along opposite edges 14 and 15. As is shown in FIGS. 2 and 3, the bandaging product 10 also includes a medical bandage 20 which is maintained in moisture-free conditions within the package 11 until use. The bandage 20 includes a substrate 21 which is encased within an outer cover 22 formed of a soft, flexible, non-woven fiber such as polypropylene or any other suitable hydrophobic fiber. Enclosing the substrate 21 within the cover 22 provides a cushioning protective layer between the skin of a patient and the substrate 21 after the bandage 20 has been applied. As discussed more fully in reference to FIGS. 8 through 12 below, the substrate 21 is formed from a single layer of a knitted, relatively open, fabric, such as fiberglass.

The package 11 includes outer, middle, and inner layers. The outer layer is preferably formed of a tear-resistant plastic film. The middle layer is preferably formed from aluminum foil and acts as a moisture resistant barrier for protecting the bandage 20 while stored within the package 11. The inner layer is preferably formed from a plastic film having thermoplastic properties suitable for heat-sealing the interior of the package 11 securely against moisture.

Figure 4:
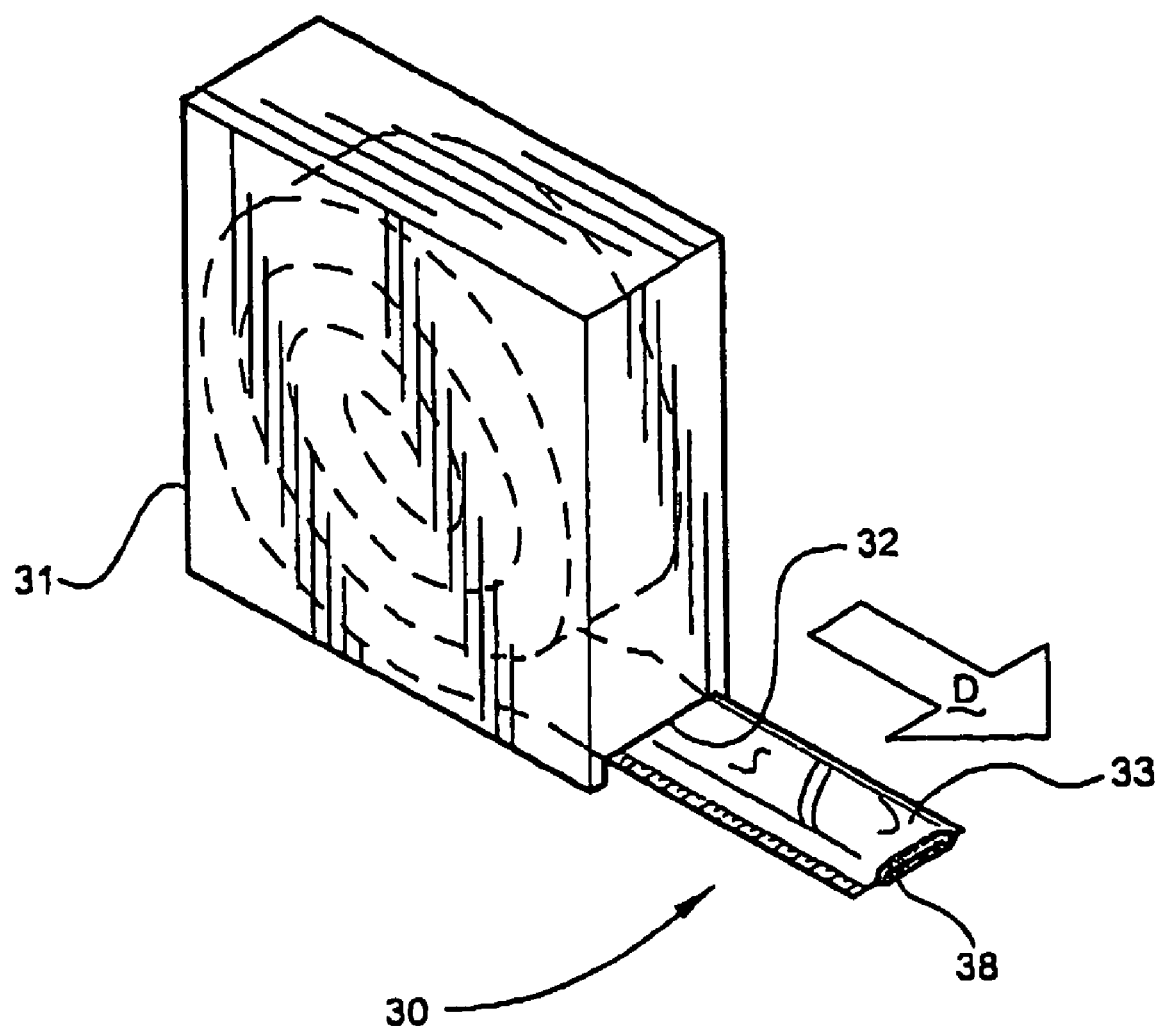
FIG. 4 is a perspective view of a medical bandaging product according to another preferred embodiment of the invention.

Referring now to FIG. 4, a medical bandaging product according to another preferred embodiment of the invention is illustrated and shown generally at reference numeral 30. Bandaging product 30 may be sold in any convenient length, such as 24 feet, and is rolled into a coil and positioned within a suitable dispenser 31. Dispenser 31 is provided with a slot 32 defined in one lower corner through which an end 33 of bandaging product 30 extends for dispensing the product 30 from the dispenser 31 in the direction "D" shown.

Figure 5:
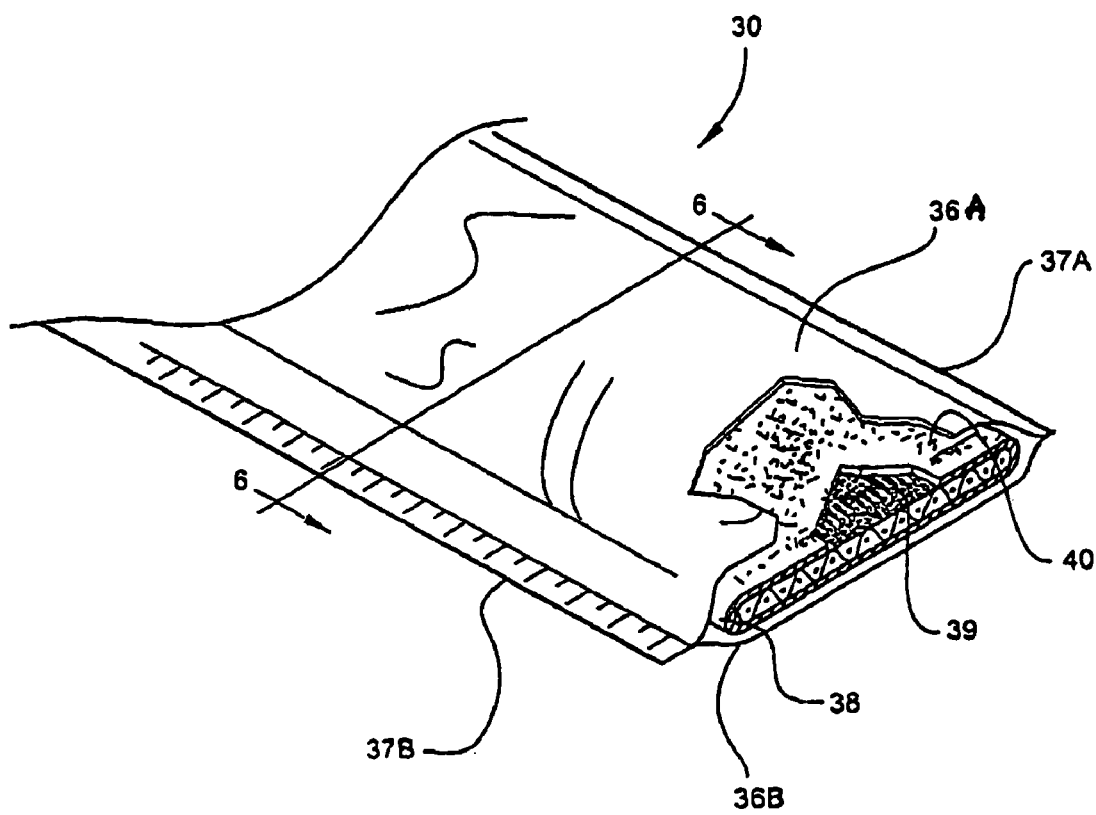
FIG. 5 is a cut-away perspective view of a length of medical bandage material according to FIG. 4.
Figure 6:
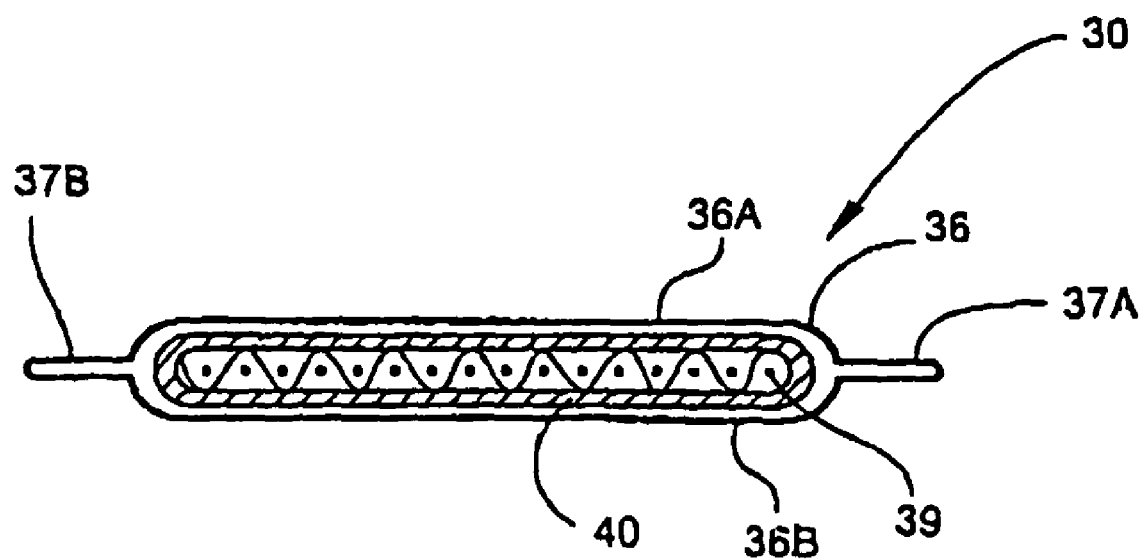
FIG. 6 is a cross-sectional view taken along Lines 6-6 of FIG. 5.

Referring now to FIG. 6, the bandaging product 30 includes an elongate medical bandaging material 35 which is packaged in moisture-free conditions in a foil sleeve 36. The sleeve 36 is formed from two laminated, elongate foil sheets 36A, 36B, which are placed in registration and heat sealed along opposing side edges 37A, 37B to form a tube having an open end 38. Each sheet 36A and 36B is formed from the same materials and includes the same components as the package 11. The bandage material 35 includes a substrate 39, which is shown in FIGS. 5 and 6 surrounded by a tubular wrapping 40 formed of the same material as the cover 12 described above in reference to FIG. 3. Enclosing the substrate 39 within the wrapping 40 protects and cushions the skin of a patient from the substrate 39 after the bandage material 35 has been applied. As discussed more fully in reference to FIGS. 7 through 9 below, the substrate 39 is formed from a single layer of a knitted relatively open fabric, such as fiberglass which is identical to that used to form substrate 21. The substrate 21 or 39 may alternatively be formed from polyester or polypropylene.

Figure 7:
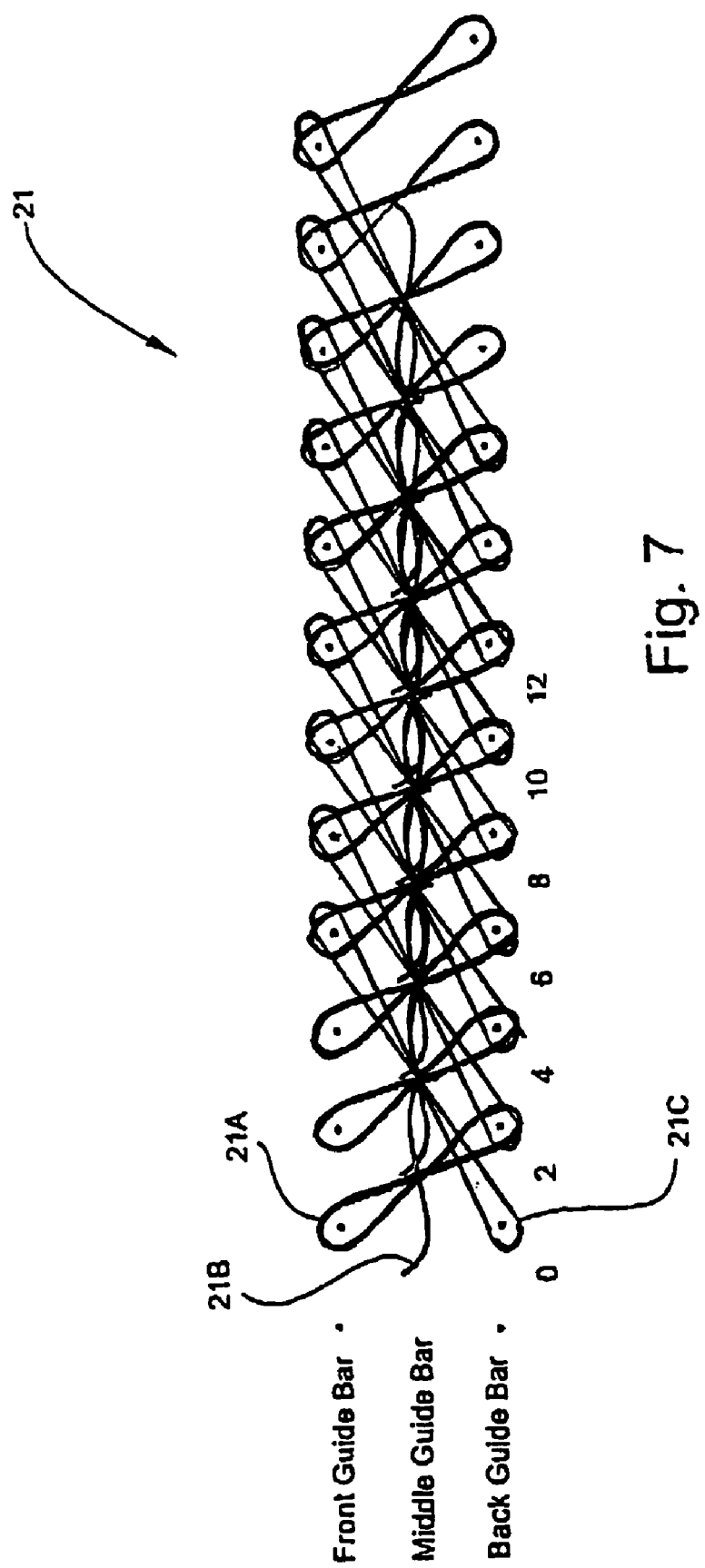
FIG. 7 is a stitch diagram showing the stitch pattern used to form the substrate according to the present invention.
Figure 8:
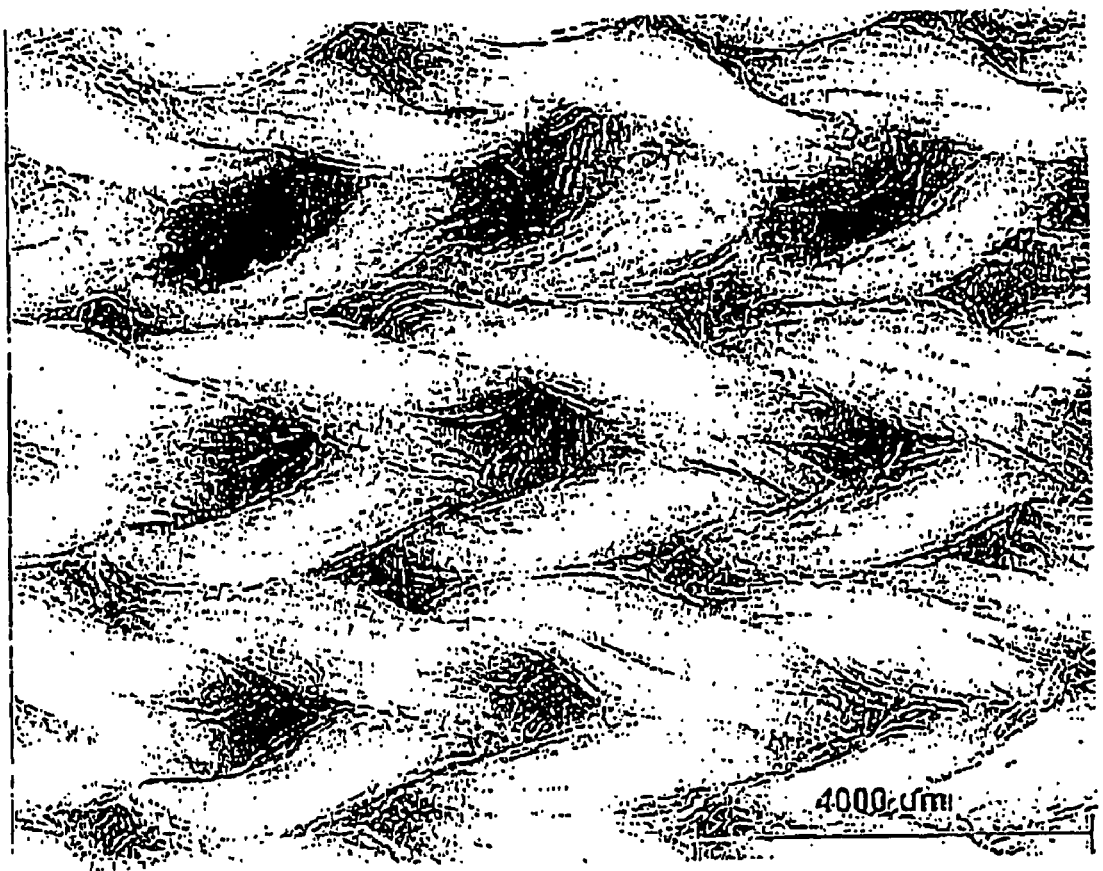
FIG. 8 is a photograph of an example of the substrate formed according to the present invention showing the front or top face of the substrate.
Figure 9:
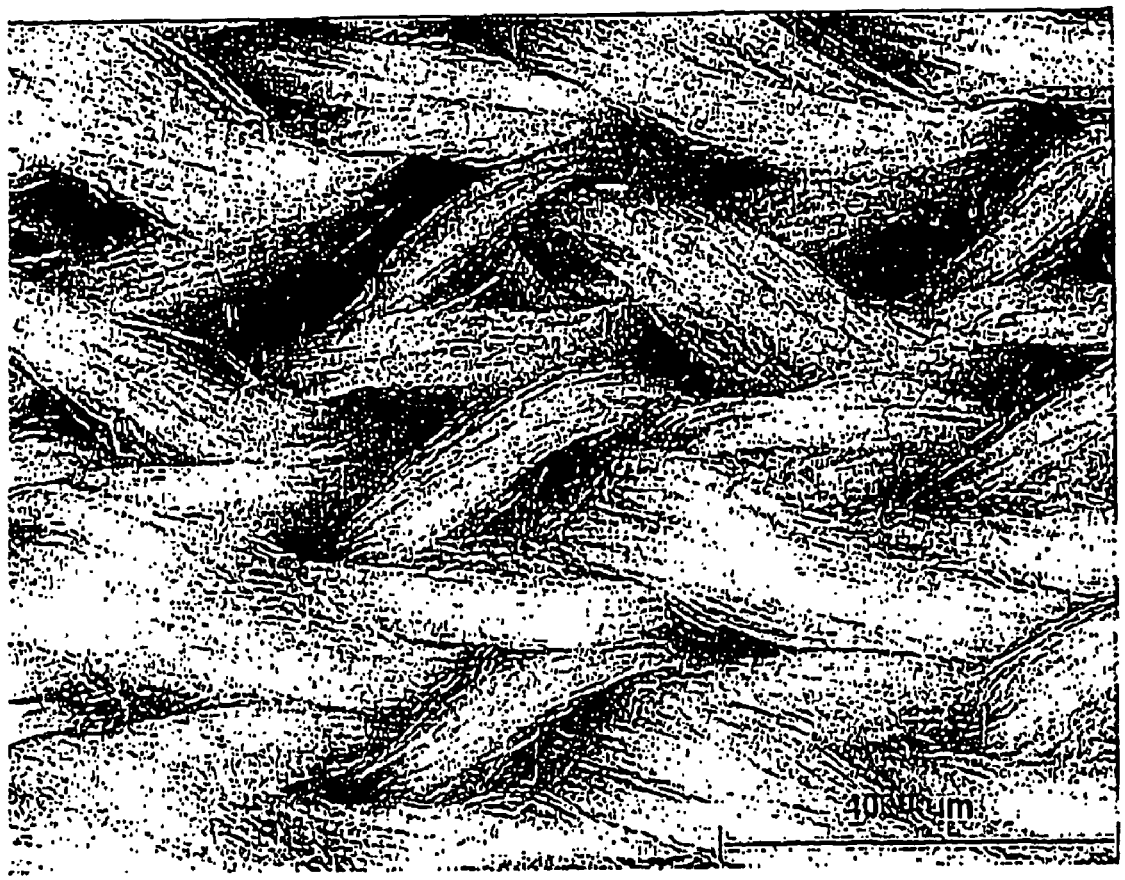
FIG. 9 is a photograph of the substrate according to the present invention showing the back or bottom face of the substrate.

Referring now to FIGS. 7 through 9, the preferred structure of the fabric used to form substrate 21 and substrate 39 is shown. The substrate of the present invention is preferably knitted on a warp knitting machine employing three guide bars. These guide bars are shown in the stitch diagram illustrated in FIG. 7 as the front, middle and back guide bars, respectively. Using substrate 21 as a representative example FIG. 7 shows the preferred stitch pattern used to form the substrate 21. Three yarns 21A, 21B, and 21C are employed. Yarn 21A is threaded on the front guide bar and has back-and-forth movement to non-adjacent needles in successive courses as indicated by the numbers (0-2/2-4). Yarns 21B and 21C are threaded on the respective middle and back guide bars and have similar movements as indicated by the numbers (0-0/4-4/8-8/4-4) and (68/0-2) respectively.

Yarns 21A, 21B, and 21C are knitted on the respective front, middle and back guide bars continuously, resulting in a three-dimensional fabric having sufficient weight to absorb adequate quantities of resin. Although any number of courses per inch may be used, a preferred number is 8 courses per inch, or 31.49 courses per 10 centimeters, with a preferred range of between 4 to 30 courses per inch, or 31.49 to 47.24 courses per 10 centimeters. A preferred number of wales is 10 per inch, or 39.37 per 10 centimeters, with a preferred range of between 6 to 12 wales per inch, or 23.62 to 47.24 wales per 10 centimeters. FIGS. 8 and 9 show photographs of the respective upper and lower surfaces of the substrate upon completion of the knitting process illustrated in FIG. 7.

The preferred substrate material used to form yarns 21A, 21B and 21C is the fiberglass material used by applicant in its ORTHOGLASS padded splint material. Specifically, each yarn 21A, 21B and 21C is preferably a yarn knitted from a textured multifilament EC9 glass yarn of 140Tex, with a preferred range of between 68Tex to 156Tex, and a flat multifilament EC9 glass yarn of 136Tex, with a preferred range of between 68Tex to 156Tex. Any suitable widths of fabric may be constructed, but conventional widths are presently 2.5 cm to 15.0 cm, in 2.5 cm increments. The finished weight of the fabric is preferably 1,750 g/m², with a preferred range of between 800 g/m² to 3,000 g/m². The finished thickness of the fabric is preferably 5.0 mm, with a preferred range of between 2.0 mm to 10.0 mm.

Other materials which may be suitable for forming the fabric used in substrate 21 or 39 include materials formed from a composition of aluminum oxide, silicone oxide and boron oxide and sold under the name NEXTEL 440 by Thermostatic Industries, Inc.

Substrates 21 and 39 are each impregnated or coated with a reactive system which remains stable when maintained in substantially moisture-free conditions blat which hardens upon exposure to sufficient moisture to form a rigid, self-supporting structure. A typical formulation of the reaction system is set forth in the following table:

Typical Formulation:

| | | |
|---|---|---|
| Isonatet 143L or Mondurt CD or Rubinatet XI168 | polyisocyanate | 50.0% |
| Pluracolt P1010 | polyol | 46.6% |
| DC-200 Silicone | defoaming agent | 0.30% |
| Benzoyl Chloride | stabilizer | 0.10% |
| Thancatt DM-70 | catalyst | 3.0% |
| | | 100% |

A complete discussion of the parameters of the reactive system, the manner of production and the variables which apply are found in U.S. Pat. No. 4,411,262, referred to above. The weight of substrate 21 or 39 after being impregnated with the reactive system is preferably 3,144 g/m, with a preferred range of between 2,490 g/m to 4,534 g/m. After undergoing the curing process, the finished weight of the impregnated substrate 21 or 39 is preferably 3,168 g/m, with a preferred range of between 3,000 g/m to 4,600 g/m.

Figure 10:
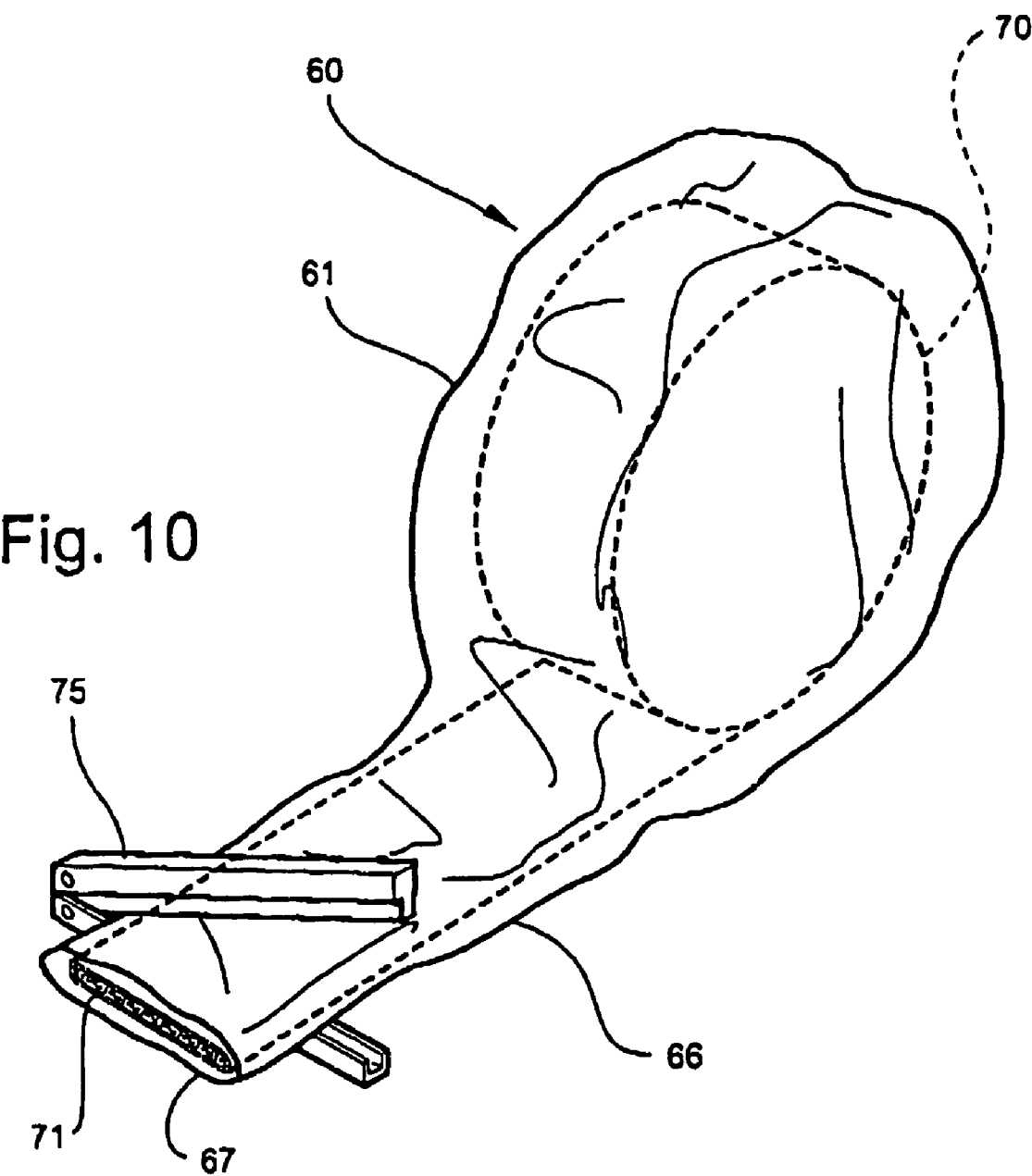
FIG. 10 is a perspective view of a medical bandaging product according to an alternative embodiment of the invention
Figure 11:
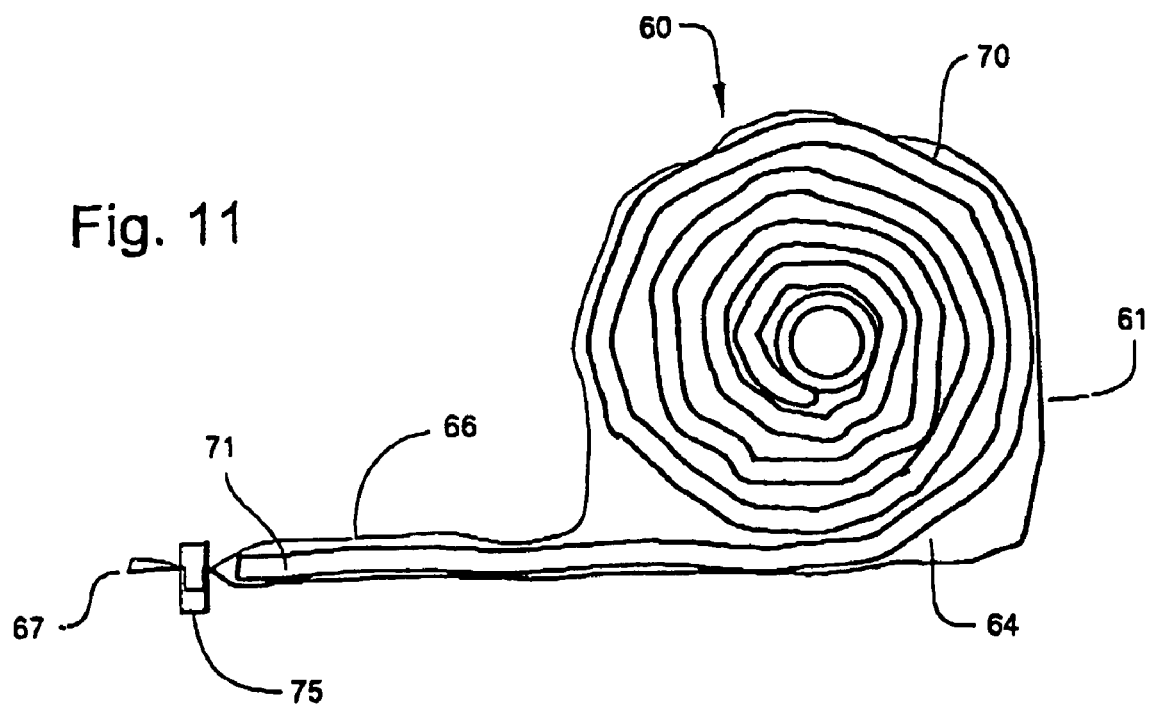
FIG. 11 is a vertical cross section of the medical bandaging product shown in FIG. 10.

Referring now to FIGS. 10 and 11, an alternative medical bandaging product is illustrated and shown generally at reference numeral 60. The bandaging product 60 includes a moisture-impervious foil bag 61 within which is contained a desired length of coiled medical bandaging material 70. Coiled bandaging material 70 includes the same components and is formed from the same materials as bandaging material 25. The foil bag 61 is constructed from the same laminated foil material used to form the pouch 11 and sleeve 36 described above. As is shown in FIG. 11, the bag 61 includes an enlarged enclosure 64 within which the medical bandaging material 70 is contained, and an elongate dispensing sleeve 66. Referring again to FIG. 10, dispensing sleeve 66 defines an open end 67 through which an end 71 of the medical bandaging material 70 is extended for dispensing. The bag 61 should relatively snugly surround the medical bandaging material 70 to retard entry of moisture into the bag 61 as the material 70 is being dispensed through the open end 67. The open end 67 of sleeve 68 is sealed with sealing means such as a clamp 75.

Figure 12:
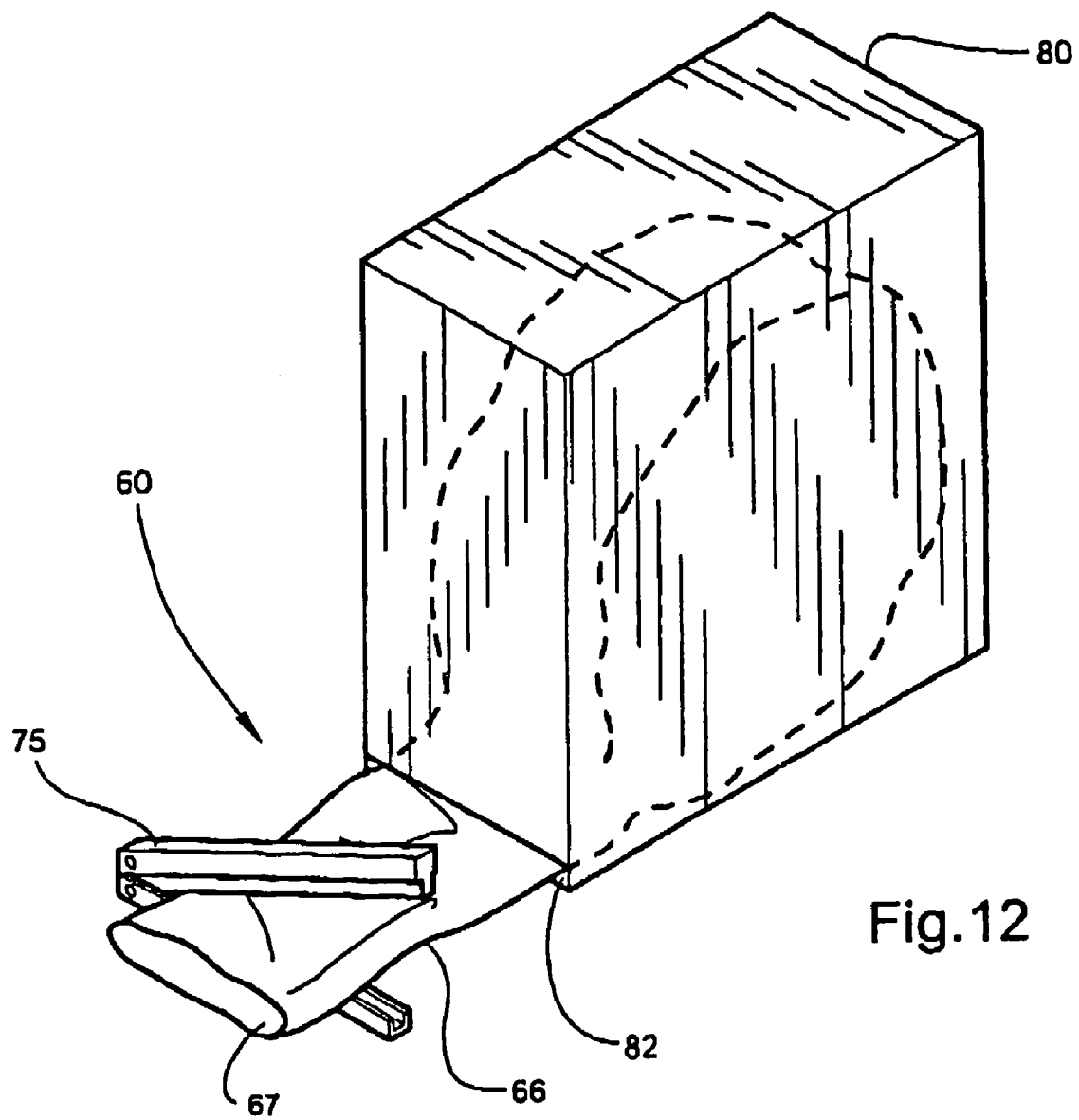
FIG. 12 is a perspective view of the medical bandaging product shown in FIG. 10 in a dispensing box, and showing a preferred embodiment of resealing the dispensing sleeve.

Referring now to FIG. 12, the bandaging product 60 is shown positioned within a suitable dispenser 80. Dispenser 80 is identical to the dispenser 31 described above in reference to FIG. 4, and includes a slot 82 defined in one lower corner through which the end 67 of sleeve 66 of the bandaging product 60 extends.

Figure 13:
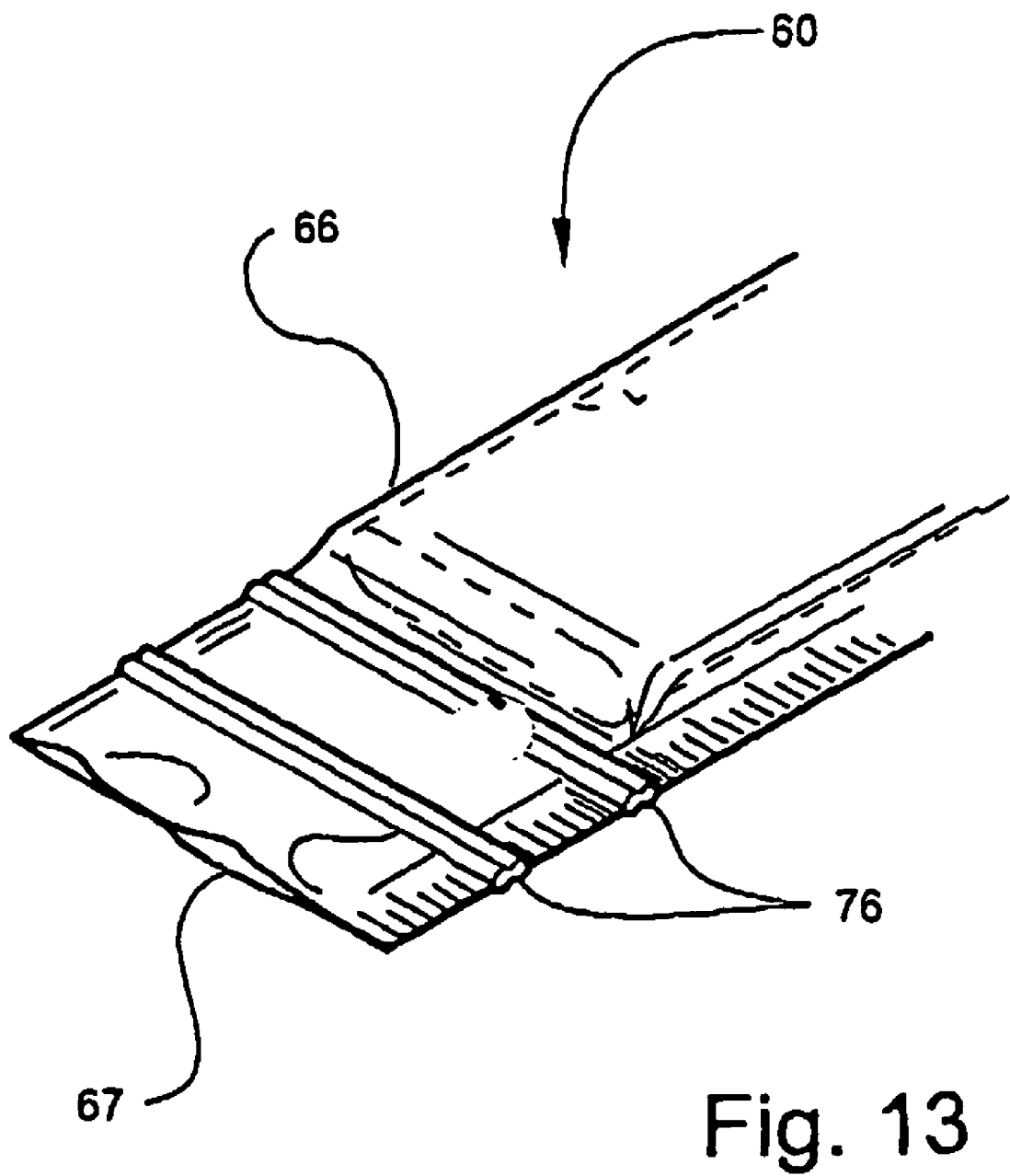
FIG. 13 is a fragmentary perspective view of one embodiment of the medical bandaging product with a zip end closure.
Figure 14:
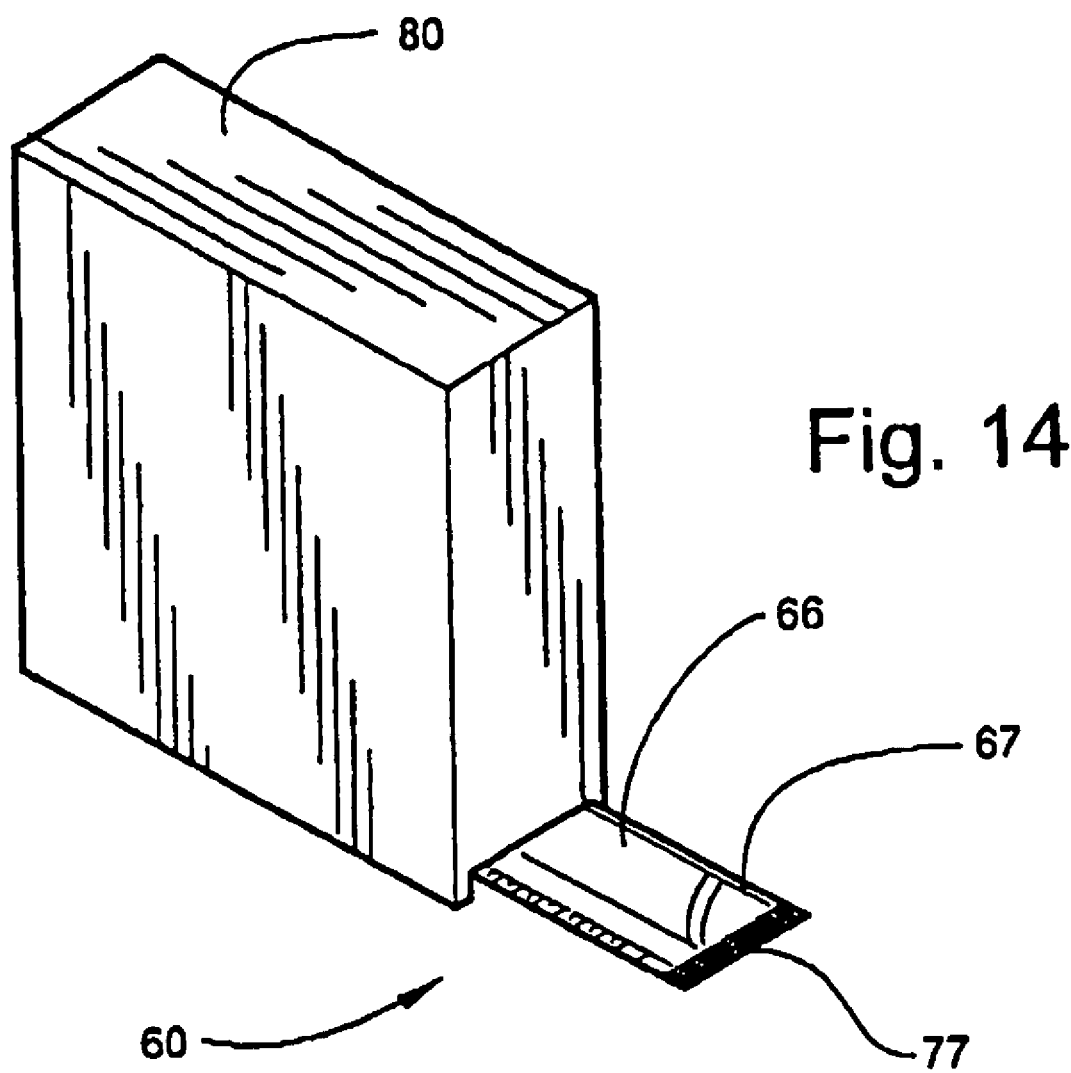
FIG. 14 is a perspective view of the medical bandaging product according to FIG. 13 showing an alternative preferred embodiment of resealing the medical bandaging product.

Referring now to FIGS. 13 and 14, alternative sealing means which may be used to seal the end 67 of the sleeve 66 include but are not limited to a zip-type closure 76 as shown in FIG. 13, or a tape strip 77 such as that shown in FIG. 14. The clamp 75, zip-type closure 76 and tape strip 77 may also be used to close the open end 38 of the sleeve 36 of the bandaging product 30 described above with reference to FIG. 5.

Other types of sealing mechanisms may also be employed to close the sleeves 36 and 66 such as, for example, a clip for holding a folded end of the sleeve 36 or 66 closed. A soft, conformable gasketing device may alternatively be used. Such a gasketing device would include spring loaded compression, leverage clamping or screw action of sufficient strength to prevent entry of moisture into sleeve 36 or 66. Another suitable device for sealing the sleeve 36 or 66 is a pair of spring loaded rollers. Such rollers roll backwards slightly when compressed, which would in turn push medical bandage material 35 and 70 back slightly into respective sleeves 36 and 66, thereby forming a better seal. Another alternative sealing means is one which pushes the medical bandage material 35 and 70 back into respective sleeves 36 and 66 a sufficient distance (approximately one inch), so that the open ends 37 and 67 may be heat sealed.

Figure 15:
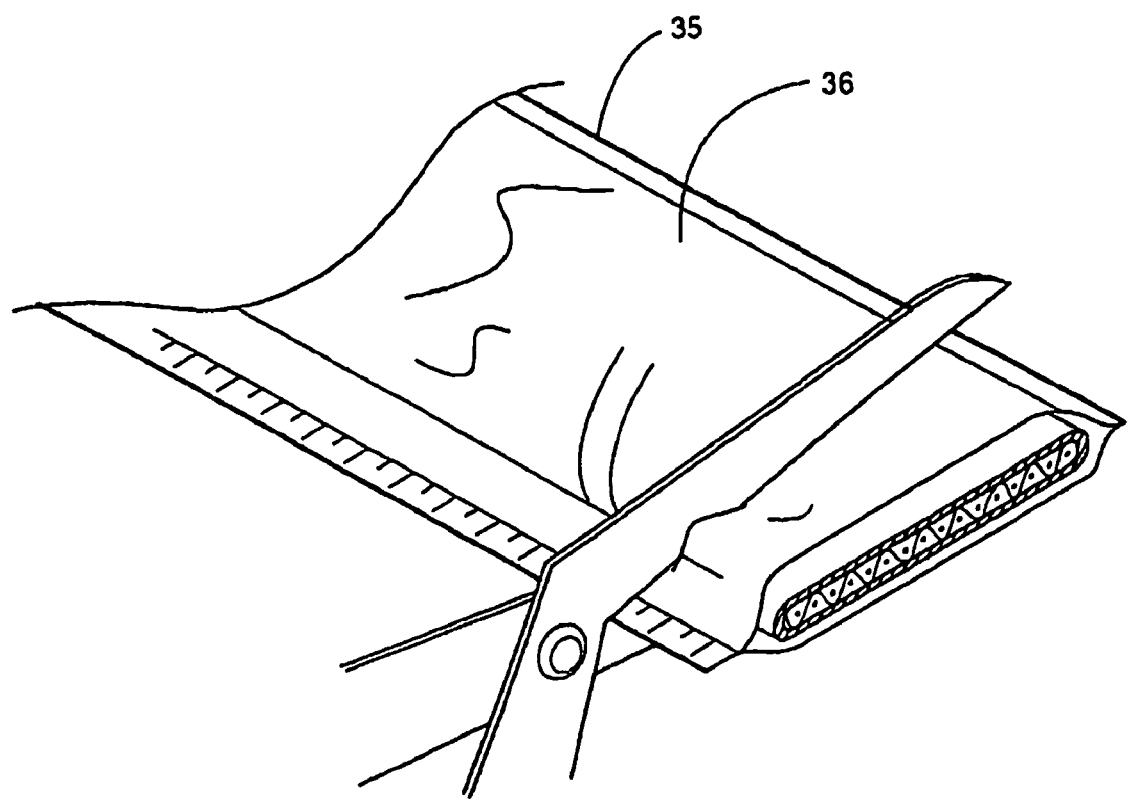
FIGS. 15 through 19 illustrate a preferred manner of preparing and applying the medical bandage material according to the present invention.

Referring now to FIGS. 15 through 19, preparation and application of the medical bandaging material of the present invention is illustrated. Using medical bandage material 35 as a representative example, as is shown in FIG. 15 the medical bandaging material 35 is first measured and cut to length using scissors or a knife. Once the appropriate length of material 35 is been cut, the sleeve 36 must be immediately resealed to prevent moisture intrusion which can harden the remaining material. See FIGS. 12 and 13.

Figure 16:
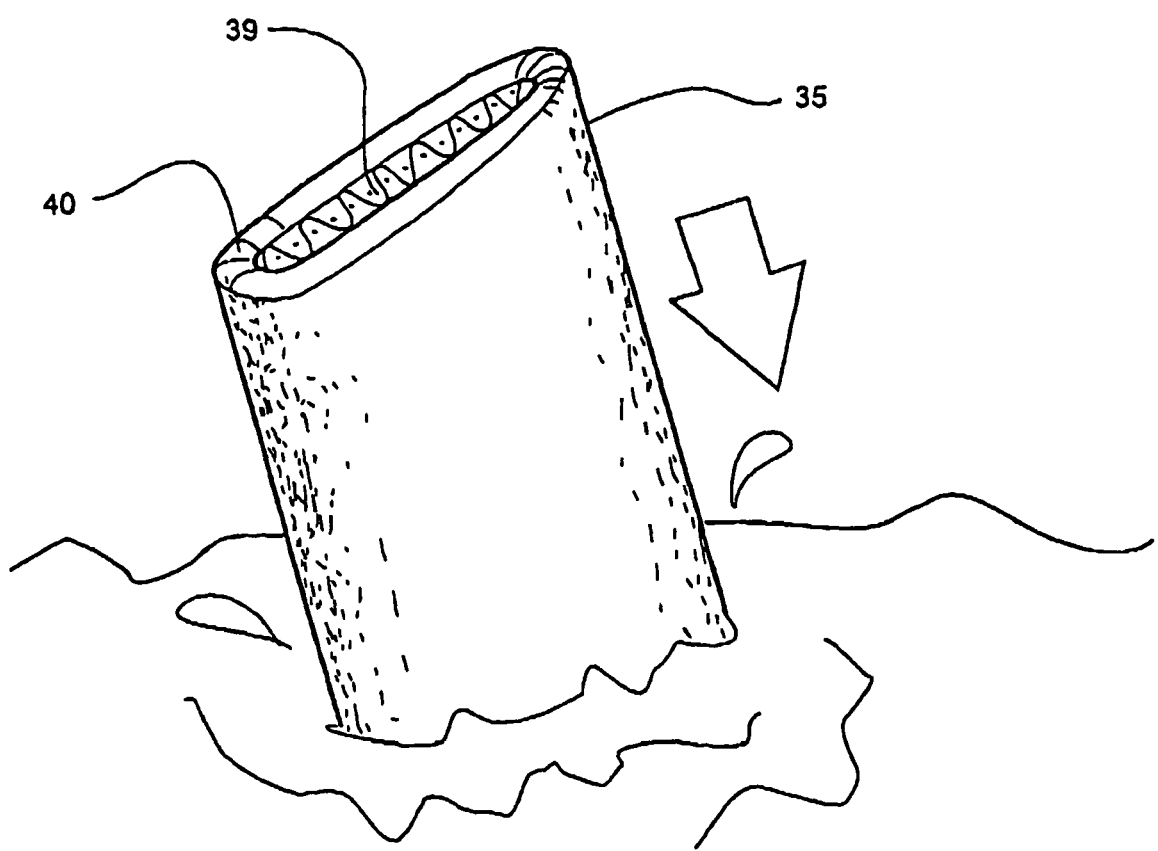
Figure 17:
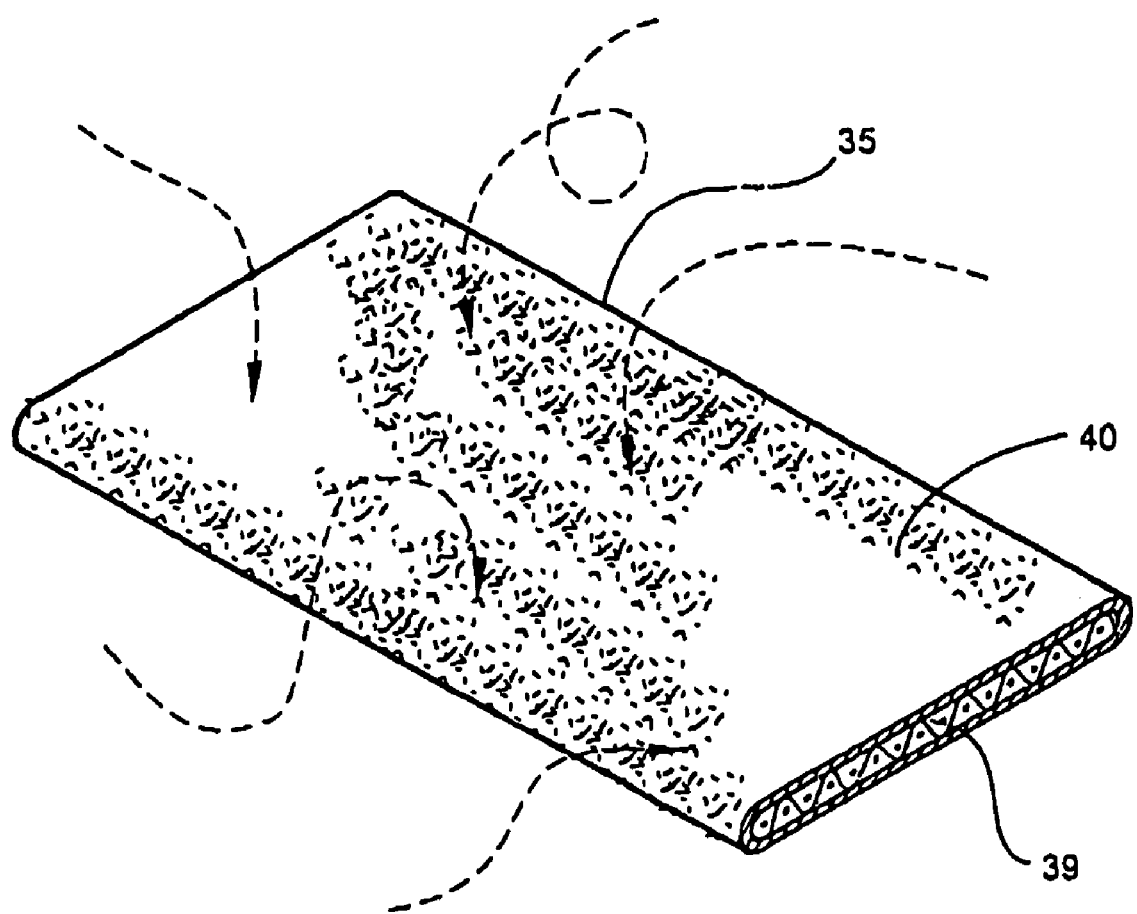

Referring now to FIG. 16, moisture curing of the resin is activated by immersing the medical bandage material 35 in water. The curing process may alternatively be activated by spraying the bandage material 35 with water. Excess moisture is then removed from the material 35 by either squeezing the material 35 or rolling the material 35 in an absorbent towel. As is shown in FIG. 17, the moisture-curing process can alternatively take place over a longer period of time by exposing the reactive system impregnated within or coated on the substrate to atmospheric moisture.

Figure 18:
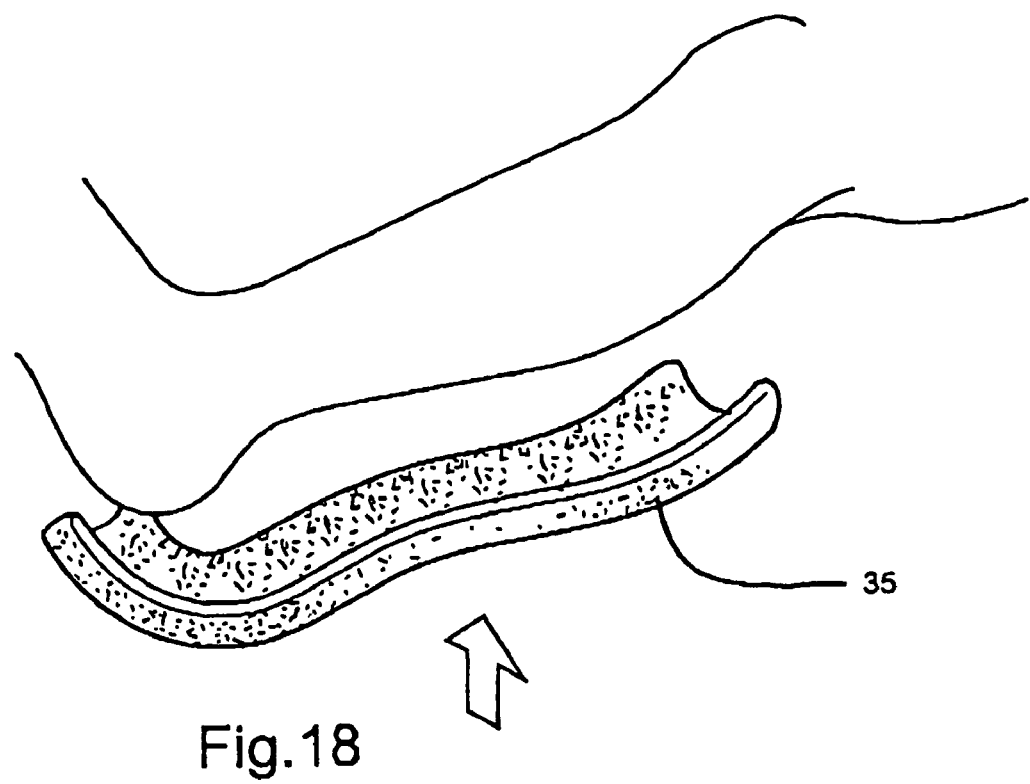
Figure 19:
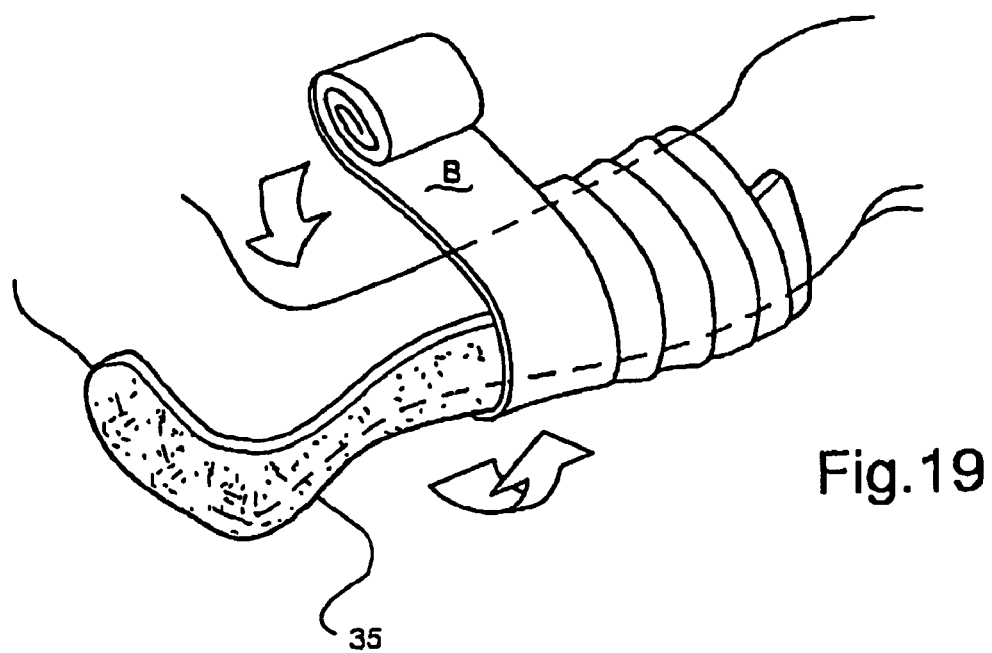

Referring now to FIGS. 18 and 19, the splint shown is commonly known as a posterior short leg splint, and is formed by molding a length of the medical bandage 35 along the calf, over the Achille's tendon and heel, and onto the foot. As is shown in FIG. 18, an appropriate length of moistened medical bandage material 35 is first formed to the shape of a body member to be immobilized. Once the bandage 35 is formed to the shape of the body member, the bandage 35 is overwrapped with a conventional elastic bandage "B", as is shown in FIG. 19.

Although the medical bandage material 35 of medical bandage product 30 is shown in FIGS. 18 and 19 in use as a posterior short leg splint, the medical bandage products 10, 30 and 60 may be utilized in any suitable medical procedure where immobilization of one or more body members is required.

A medical bandaging product and material formed of a moisture-curable plastic material, a method for constructing such an improved medical bandage, and a method of constructing and applying an improved bandaging product is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

The invention claimed is:
1. A medical bandaging product comprising:
   (a) an enclosure formed of a moisture-impervious material sealable to prevent entry of moisture; and
   (b) a medical bandage material positioned in said enclosure and sealed therein against entry of moisture until use, said medical bandage material comprising:
      (i) a substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;
      (ii) a reactive system impregnated into or coated onto said substrate, said system remaining stable when maintained in substantially moisture-free conditions and hardening upon exposure to sufficient moisture to cooperate with said three-dimensional structure to form a rigid, self supporting structure; and
      (iii) a soft, flexible protective wrapping enclosing the substrate along its length for providing a cushioning barrier interposed between the substrate and a patient when said medical bandage material is in use.

2. A medical bandaging product according to claim 1, wherein said moisture-impervious material comprises an aluminum foil laminate having an outer tear resistant layer, a central aluminum foil layer and an inner heat sealable plastic layer.

3. A medical bandaging product according to claim 1, wherein said protective wrapping enclosing the substrate comprises a fibrous nonwoven material.

4. A medical bandaging product according to claim 3, wherein said protective wrapping enclosing the substrate comprises a nonwoven polypropylene sheet folded along its longitudinal axis to define an envelope within which the substrate is positioned.

5. A medical bandaging product according to claim 1, wherein the substrate has a thickness of about 5 mm.

6. A medical bandaging product as claimed in claim 1 in roll form for being dispensed in suitable lengths for a given medical use, in which:
   (a) the enclosure comprises an elongate sleeve;
   (b) the medical bandage material is of substantially the same length as the sleeve in a single length along the length of the sleeve, the medical bandage material being positioned in the enclosure for being dispensed in desired use length from said sleeve, the sleeve being adapted for being resealed to prevent moisture from entering the enclosure.

7. A medical bandaging product according to claim 6, wherein said sleeve and the medical bandage material positioned therein are formed into a coil, thereby creating the roll form of the medical bandaging product.

8. A medical bandaging product according to claim 7, and including a dispenser within which said roll or coil is contained.

9. A medical bandaging product according to claim 8, wherein said dispenser comprises a container within which the roll or coil is positioned, said container defining a slot therein in which a leading end of the coil may be positioned and through which the sleeve and the medical bandage positioned therein are dispensed as needed.

10. A medical bandaging product according to claim 1, wherein the substrate has a thickness of between about 2 mm and 10 mm.

11. A medical bandaging product according to claim 1, wherein said fabric includes three yarns, the first yarn being threaded on a front guide bar and having a back-and-forth pattern between non-adjacent needle positions in successive courses, and the second and third yarns threaded onto middle and back guide bars, respectively, having similar movements, the three yarns continuously knitted on the front, middle, and back guide bars.

12. A medical bandaging product according to claim 1, wherein said at least one yarn is a continuous inlaid stitch extending from the first major outer surface to the second major outer surface along an entire width of the substrate.

13. A method of constructing a medical bandaging product, comprising the steps of:
   (a) providing a substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;
   (b) impregnating into or coating onto the substrate a reactive system which remains stable when maintained in substantially moisture-free conditions and hardens upon exposure to sufficient moisture to cooperate with said three-dimensional structure to form a rigid, self-supporting structure;
   (c) positioning within said elongate sleeve a length of said elongate medical bandage material having generally the same length as the sleeve and extending along the length of the sleeve in a single layer; and
   (d) sealing the sleeve to prevent entry of moisture therein until use.

14. A method of constructing a medical bandaging product as claimed in claim 13, comprising providing an elongate sleeve and an elongate medical bandage material.

15. A method of constructing a medical bandaging product according to claim 14 and including the step of rolling the sleeve with the medical bandage material therein into a coil.

16. A method of constructing a medical bandaging product according to claim 15, and including the step of packaging said coil in a dispenser.

17. A method of constructing a medical bandaging product according to claim 16, wherein said dispenser comprises a box provided with a slot therein for feeding a desired length of the medical bandaging material therethrough.

18. A method of constructing a medical bandaging product according to claim 13, and including the step of resealing the sleeve against entry of moisture after a predetermined length of the bandaging material has been dispensed for use to prevent hardening of the substrate remaining in the sleeve.

19. A method of utilizing a medical bandaging product, comprising the steps of:
   (a) providing a substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;
   (b) impregnating into or coating onto said substrate a reactive system which remains stable when maintained in substantially moisture-free conditions and hardens upon exposure to sufficient moisture to cooperate with said three-dimensional structure to form a rigid, self-supporting structure;
   (c) positioning the medical bandage material within said elongate sleeve;
   (d) sealing the sleeve to prevent entry of moisture until use;
   (e) removing the medical bandage material from the sleeve immediately prior to use;
   (f) wetting the substrate to activate the reactive system; and
   (g) applying the medical bandaging material to a patient.

20. A method according to claim 19, and including the step of overwrapping the medical bandaging material with an elastic bandage to maintain the medical bandaging material in close conformity with the patient during the curing of the moisture-curable resin.

21. A medical bandaging product having a predetermined length suitable for a given medical use, comprising:
   (a) an enclosure formed of a moisture-impervious material sealable to prevent entry of moisture; and
   (b) a medical bandage material positioned in said enclosure and sealed therein against entry of moisture until use, said medical bandage material comprising:
      (i) providing a substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;
      (ii) a reactive system impregnated into or coated onto said substrate, said system remaining stable when maintained in substantially moisture-free conditions and hardening upon exposure to sufficient moisture to cooperate with said three-dimensional structure to form a rigid, self supporting structure; and (iii) a soft, flexible protective wrapping enclosing the substrate along its length for providing a cushioning barrier interposed between the substrate and a patient when said medical bandage material is in use.

22. A medical bandaging product in roll form for being dispensed in predetermined lengths suitable for a given medical use, comprising:

(a) an elongate sleeve formed of moisture-impervious material and sealable to prevent entry of moisture;

(b) an elongate medical bandage material substantially the same length as the sleeve and positioned in said sleeve in a single length along the length of the sleeve and sealed therein against entry of moisture until use, said medical bandage material comprising:

a substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;

(ii) a reactive system impregnated into or coated onto said substrate, said system remaining stable when maintained in substantially moisture-free conditions and hardening upon exposure to sufficient moisture to cooperate with said three-dimensional structure to form a rigid, self-supporting structure; and (iii) a soft, flexible protective wrapping enclosing the substrate along its length for providing a cushioning barrier interposed between the substrate and a patient when said medical bandage material is in use;

the medical bandage material being positioned in the enclosure for being dispensed in a desired use length from said sleeve, the sleeve adapted for being resealed to prevent moisture from entering the enclosure.

23. A method of constructing a medical bandaging product, comprising the steps of:

(a) providing an elongate, moisture-impervious sleeve and an elongate medical bandage material comprised of a substrate enclosed within a protective wrapping, said substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;

(b) impregnating into or coating onto the substrate a reactive system which remains stable when maintained in substantially moisture-free conditions and hardens upon exposure to sufficient moisture to cooperate with said three-dimensional structure to form a rigid, self-supporting structure;

(c) positioning within said elongate sleeve a length of said elongate medical bandage material having generally the same length as the sleeve and extending along the length of the sleeve in a single layer; and (d) sealing the sleeve to prevent entry of moisture therein until use.

24. A method of constructing a medical bandaging product, comprising the steps of:

(a) providing a moisture impervious sleeve and a substrate for being enclosed within a protective wrapping, said substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;

(b) impregnating into or coating onto said substrate a reactive system which remains stable when maintained in substantially moisture-free conditions and hardens upon exposure to sufficient moisture to cooperate with said three-dimensional structure to form a rigid, self-supporting structure;

(c) positioning the coated or impregnated substrate within the protective wrapping to form a medical bandage material;

(d) positioning within the sleeve a length of said medical bandage material having generally the same length as the sleeve and extending along the length of the sleeve in a single layer; and (e) sealing the sleeve to prevent entry of moisture until use.

25. A method of utilizing a medical bandaging product, comprising the steps of:

(a) providing an enclosure and a medical bandage material comprised of a substrate enclosed within a protective wrapping, said substrate comprising providing a substrate comprising a knitted fabric layer that defines a major upper surface and a major lower surface having the same knit pattern in both the upper and lower surfaces, the knitted fabric layer including spaced apart edges and a plurality of interconnected knitted fabric yarns knitted such that at least one yarn extends from the major upper surface to the major lower surface along a width of the substrate in a back-and-forth pattern between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate;

(b) impregnating into or coating onto said substrate a reactive system which remains stable when maintained in substantially moisture-free conditions and hardens upon exposure to sufficient moisture to cooperate with said three-dimensional structure to form a rigid, self-supporting structure;

(c) positioning the elongate medical bandage material within said elongate sleeve;

(d) sealing the sleeve to prevent entry of moisture until use;

(e) removing the medical bandage material from the sleeve immediately prior to use;

(f) wetting the substrate to activate the reactive system; and (g) applying the medical bandaging material to a patient.

* * * * *